United States Patent
Osawa et al.

(10) Patent No.: US 11,394,911 B2
(45) Date of Patent: Jul. 19, 2022

(54) IMAGING SYSTEM

(71) Applicant: OLYMPUS CORPORATION, Hachioji (JP)

(72) Inventors: Masato Osawa, Tokyo (JP); Keisuke Ogawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/190,838

(22) Filed: Mar. 3, 2021

(65) Prior Publication Data

US 2021/0185254 A1 Jun. 17, 2021

Related U.S. Application Data

(63) Continuation of application No. PCT/JP2019/000286, filed on Jan. 9, 2019.

(51) Int. Cl.
*A61B 1/00* (2006.01)
*H04N 5/369* (2011.01)
(Continued)

(52) U.S. Cl.
CPC ....... *H04N 5/3698* (2013.01); *A61B 1/00006* (2013.01); *A61B 1/00009* (2013.01);
(Continued)

(58) Field of Classification Search
CPC .............. H04N 5/3698; H04N 17/002; H04N 2005/2255; H04N 5/232; H04N 7/18;
(Continued)

(56) References Cited

U.S. PATENT DOCUMENTS

| | | | | |
|---|---|---|---|---|
| 2010/0022833 A1* | 1/2010 | Nagase | .................. | A61B 1/041 600/118 |
| 2014/0135579 A1* | 5/2014 | Brichard | ................ | A61B 34/30 600/117 |

(Continued)

FOREIGN PATENT DOCUMENTS

| | | |
|---|---|---|
| JP | 2009-22579 A | 2/2009 |
| JP | 2018-94235 A | 6/2018 |

(Continued)

OTHER PUBLICATIONS

International Search Report dated Apr. 2, 2019, issued in counterpart International Application No. PCT/JP2019/000286 (2 pages, including Japanese original and English translation).

*Primary Examiner* — Howard D Brown, Jr.
(74) *Attorney, Agent, or Firm* — WHDA, LLP

(57) ABSTRACT

In an imaging system according to an embodiment, a camera unit and an information-processing unit are connected to each other by differential-signal transmission lines. The camera unit includes a solid-state imaging device and an output driver. The solid-state imaging device is configured to operate on the basis of a power source voltage higher than a substrate voltage and generate imaging data. The output driver is configured to output a differential signal of the imaging data to the differential-signal transmission lines. The information-processing unit includes a voltage generator and a de-emphasis circuit. The voltage generator is configured to generate a reference voltage higher than the substrate voltage and lower than the power source voltage. The de-emphasis circuit is configured to control an amplitude of the differential signal by using the substrate voltage and the reference voltage.

10 Claims, 7 Drawing Sheets

(51) Int. Cl.
*A61B 1/018* (2006.01)
*A61B 1/045* (2006.01)
*A61B 1/05* (2006.01)
*A61B 1/12* (2006.01)
*H04N 17/00* (2006.01)
*A61B 17/32* (2006.01)
*A61B 18/14* (2006.01)

(52) U.S. Cl.
CPC .......... *A61B 1/00057* (2013.01); *A61B 1/018* (2013.01); *A61B 1/045* (2013.01); *A61B 1/051* (2013.01); *A61B 1/128* (2013.01); *H04N 17/002* (2013.01); *A61B 17/320068* (2013.01); *A61B 18/14* (2013.01); *A61B 2017/320082* (2017.08)

(58) Field of Classification Search
CPC ............ A61B 1/00006; A61B 1/00009; A61B 1/00057; A61B 1/018; A61B 1/045; A61B 1/051; A61B 1/128; A61B 17/320068; A61B 18/14; A61B 2017/320082
See application file for complete search history.

(56) References Cited

U.S. PATENT DOCUMENTS

2017/0172387 A1* 6/2017 Matsui ................... A61B 1/063
2021/0045718 A1* 2/2021 Moore ................ A61B 8/4494

FOREIGN PATENT DOCUMENTS

JP  6427303 B1  11/2018
WO  2007/004428 A1  1/2007

* cited by examiner

IMAGING SYSTEM

The present application is a continuation application based on International Patent Application No. PCT/JP2019/000286 filed on Jan. 9, 2019, the content of which is incorporated herein by reference.

BACKGROUND OF THE INVENTION

Field of the Invention

The present invention relates to an imaging system.

Description of Related Art

An imaging system (endoscope system) that executes communication between a camera unit (imaging device) and an information-processing unit by using a differential-signal transmission line including a de-emphasis circuit has been considered. For example, Japanese Unexamined Patent Application, First Publication No. 2018-094235 discloses an imaging system in which a filter corresponding to a de-emphasis circuit is provided in an information-processing unit.

SUMMARY OF THE INVENTION

According to a first aspect of the present invention, an imaging system includes a camera unit and an information-processing unit. The camera unit and the information-processing unit are connected to each other by differential-signal transmission lines. The camera unit includes a solid-state imaging device and an output driver. The solid-state imaging device is configured to operate on the basis of a power source voltage higher than a substrate voltage and generate imaging data. The output driver is configured to output a differential signal of the imaging data to the differential-signal transmission lines. The information-processing unit includes a voltage generator and a de-emphasis circuit. The voltage generator is configured to generate a reference voltage higher than the substrate voltage and lower than the power source voltage. The de-emphasis circuit is configured to control an amplitude of the differential signal by using the substrate voltage and the reference voltage.

According to a second aspect of the present invention, in the first aspect, the camera unit may include a test-data generation circuit configured to output test data. The camera unit may be configured to output a differential signal of the test data in addition to the differential signal of the imaging data to the differential-signal transmission lines through the output driver. The information-processing unit may include an error determination circuit configured to determine an error of the test data. The error determination circuit may be configured to change the reference voltage to be generated by the voltage generator in accordance with a determination result of the error.

According to a third aspect of the present invention, in the second aspect, the error determination circuit may be configured to increase the reference voltage to be generated by the voltage generator when an error rate is greater than a predetermined value.

According to a fourth aspect of the present invention, in the second aspect, the error determination circuit may be configured to reduce the reference voltage to be voltage having a value less than a predetermined value when the error determination circuit determines that an error of the imaging data has occurred. The camera unit may be configured to execute a resetting operation or an error-recovery operation in a case in which the camera unit determines that the reference voltage is reduced to be the voltage having the value less than the predetermined value.

According to a fifth aspect of the present invention, in the fourth aspect, the camera unit may include a medium-voltage measurement circuit configured to measure a medium voltage of the differential-signal transmission lines. The camera unit may be configured to execute the resetting operation or the error-recovery operation when the medium voltage is less than a value associated with the predetermined value.

According to a sixth aspect of the present invention, in the fifth aspect, the camera unit may be configured to determine contents of the resetting operation or the error-recovery operation in accordance with a length of a period during which the medium voltage is less than the value associated with the predetermined value.

According to a seventh aspect of the present invention, in any one of the first to sixth aspects, the camera unit may further include a reception driver configured to receive data from the information-processing unit through the differential-signal transmission lines. The imaging system may be configured to switch between a downlink communication mode of transmitting data from the output driver to the information-processing unit and an uplink communication mode of transmitting data from the information-processing unit to the reception driver. The information-processing unit may be configured to set the reference voltage to be generated by the voltage generator to a first value in the downlink communication mode. The information-processing unit may be configured to set the reference voltage to be generated by the voltage generator to a second value different from the first value in the uplink communication mode.

According to an eighth aspect of the present invention, in any one of the first to seventh aspects, the information-processing unit may be configured to connect to or communicate with an external treatment device. The information-processing unit may be configured to set the reference voltage to be generated by the reference-voltage generator when the external treatment device is operating to be higher than the reference voltage when the external treatment device is not operating.

According to a ninth aspect of the present invention, in any one of the first to eighth aspects, the camera unit may be configured to transmit data including temperature information of the camera unit acquired by a temperature sensor to the information-processing unit. The information-processing unit is configured to reduce the reference voltage when the measured temperature is higher than a predetermined temperature.

According to a tenth aspect of the present invention, in any one of the first to ninth aspects, the camera unit may further include a reception driver configured to receive data from the information-processing unit through the differential-signal transmission lines. The imaging system may be configured to switch between a downlink communication mode of transmitting data from the output driver to the information-processing unit and an uplink communication mode of transmitting data from the information-processing unit to the reception driver. The output driver may include a first switch, a second switch, a third switch, and a fourth switch. The output driver may be configured to simultaneously turn on or off the first switch and the third switch and simultaneously turn on or off the second switch and the fourth switch so as to output the imaging data as the differential signal in the downlink communication mode.

The output driver may be configured to turn on the first switch and the second switch and turn off the third switch and the fourth switch in the uplink communication mode so as to form a transmission path of a differential signal of the data transmitted from the information-processing unit to the reception driver and so as to cause the first switch and the second switch to be part of a termination resistance in the uplink communication mode.

DETAILED DESCRIPTION OF THE INVENTION

Figure 1:
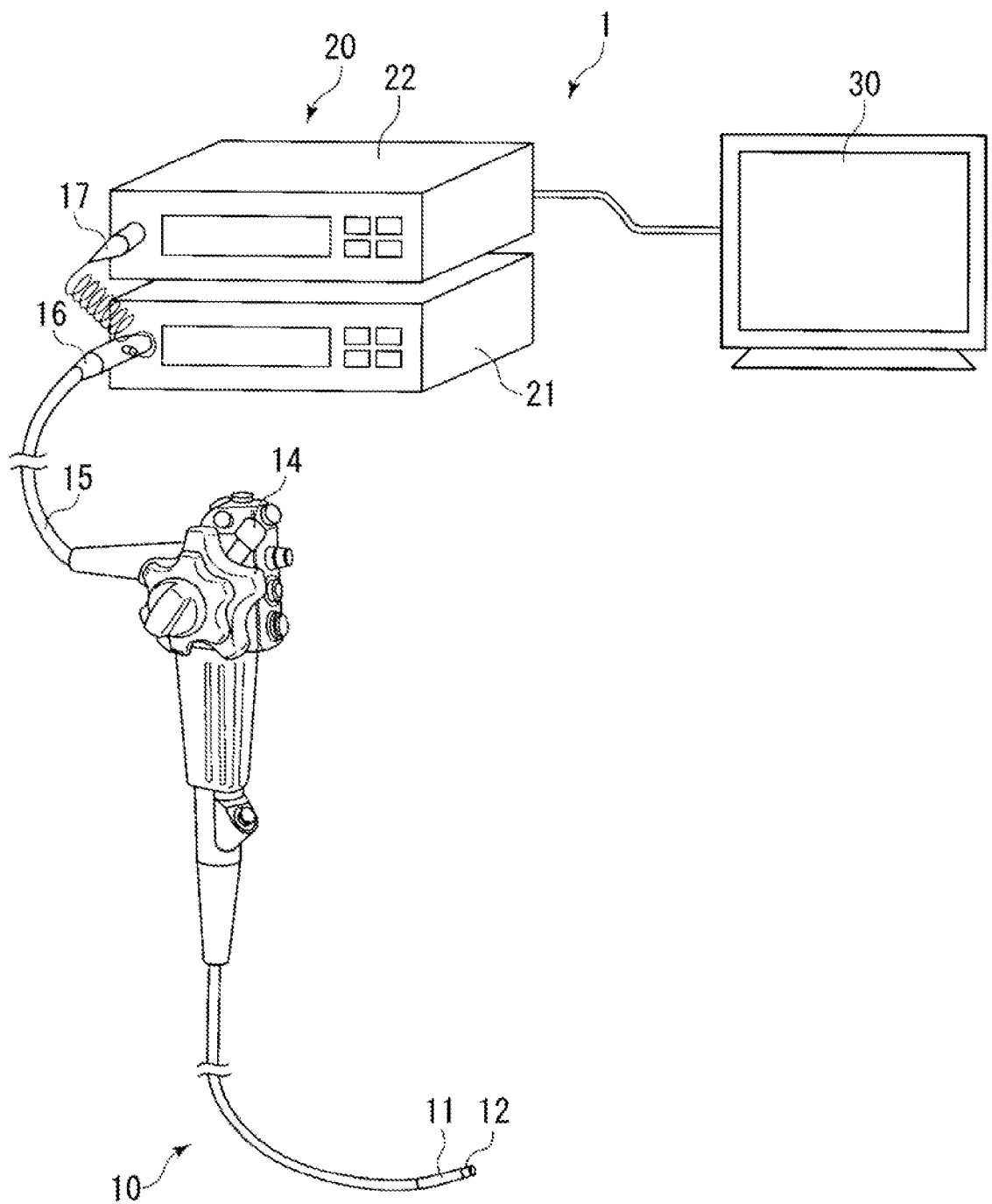
FIG. 1 is a diagram showing a schematic configuration of an endoscope system including an endoscope according to an embodiment of the present invention.

Hereinafter, embodiments of the present invention will be described with reference to the drawings. FIG. 1 is a diagram showing a schematic configuration of an endoscope system including an endoscope according to an embodiment of the present invention. The endoscope system (imaging system 1) shown in FIG. 1 includes a scope 10, a controller 20, and a monitor 30. The scope 10 transmits imaging data of the inside of a body of a subject to an image processor 22 of the controller 20. The image processor 22 processes the imaging data transmitted from the scope 10. The monitor 30 displays a picture on the basis of the imaging data processed by the controller 20.

The scope 10 functioning as an endoscope in the embodiment includes an insertion unit 11, an operation unit 14, a cable 15, a connector 16, and a connector 17.

The insertion unit 11 is a portion to be inserted into the inside of the body of the subject. An imaging device 12 (camera unit 2 described later) is provided inside the distal end of the insertion unit 11. The imaging device 12 is a CMOS sensor or a CCD sensor, images the inside of the body of the subject, and generates imaging data related to the subject. The camera unit 2 will be described in detail later. In addition, the insertion unit 11 is configured to emit illumination light from the distal end.

The insertion unit 11 is configured so as to include a portion designed to curve by receiving an operation of an operation knob of the operation unit 14 by an operator such as a doctor and include a portion that passively curves by external force regardless of the operation of the operation unit 14.

The operation unit 14 connects the insertion unit 11 and the cable 15 together. The operation unit 14 includes an RL knob for performing an operation of curving the insertion unit 11 in the right and left directions and a UD knob for performing an operation of curving the insertion unit 11 in the up and down directions. In addition, the operation unit 14 includes various switches.

A light guide is formed inside the insertion unit 11, the operation unit 14, and the cable 15. This light guide is connected to a light source device 21 of the controller 20 by the connector 16 provided in the base end of the cable 15. In addition, various signal lines including a video signal line and the like as a transmission line for transmitting the imaging data are formed inside the insertion unit 11, the operation unit 14, and the cable 15. These signal lines, in other words, signal lines including a differential-signal transmission line described later are connected to the image processor 22 of the controller 20 by the connector 17 connected to the connector 16. Furthermore, channels are provided for the purpose of passing from the operation unit 14 to the insertion unit 11. The channels are provided so that various treatment tools including an ultrasonic coagulation-and-incision apparatus such as an ultrasonic scalpel, a high-frequency current generator such as an electric scalpel, and the like are inserted to the distal end of the insertion unit 11. With these channels provided, observation using an endoscope and treatment using treatment tools can be simultaneously performed.

All the components of an information-processing unit 3 of the embodiment, including a DSP 303 and the like, may be included in the image processor 22. Details of the information-processing unit 3 will be described later. Some of the components of the information-processing unit 3 such as a de-emphasis circuit 301 and a reference-voltage generator 304 may be included in a portion, for example, the connector 16 and the connector 17 different from the image processor 22.

The light source device 21 includes a light source such as a white LED and emits illumination light. The illumination light emitted from the light source device 21 is delivered to the distal end of the insertion unit 11 by the light guide and is emitted from the distal end of the insertion unit 11. In this way, the inside of the subject is illuminated.

The information-processing unit 3 as an external signal-processing apparatus of the imaging device 12 (camera unit 2 described later) processes imaging data acquired in the imaging device 12 of the insertion unit 11. This processing includes processing of converting imaging data on which gradation correction or the like has been performed into a format that the monitor 30 is able to display.

The monitor 30 is, for example, a crystal liquid monitor. The monitor 30 displays various pieces of information and pictures on the basis of the imaging data processed by the information-processing unit 3.

First Embodiment

Figure 2:
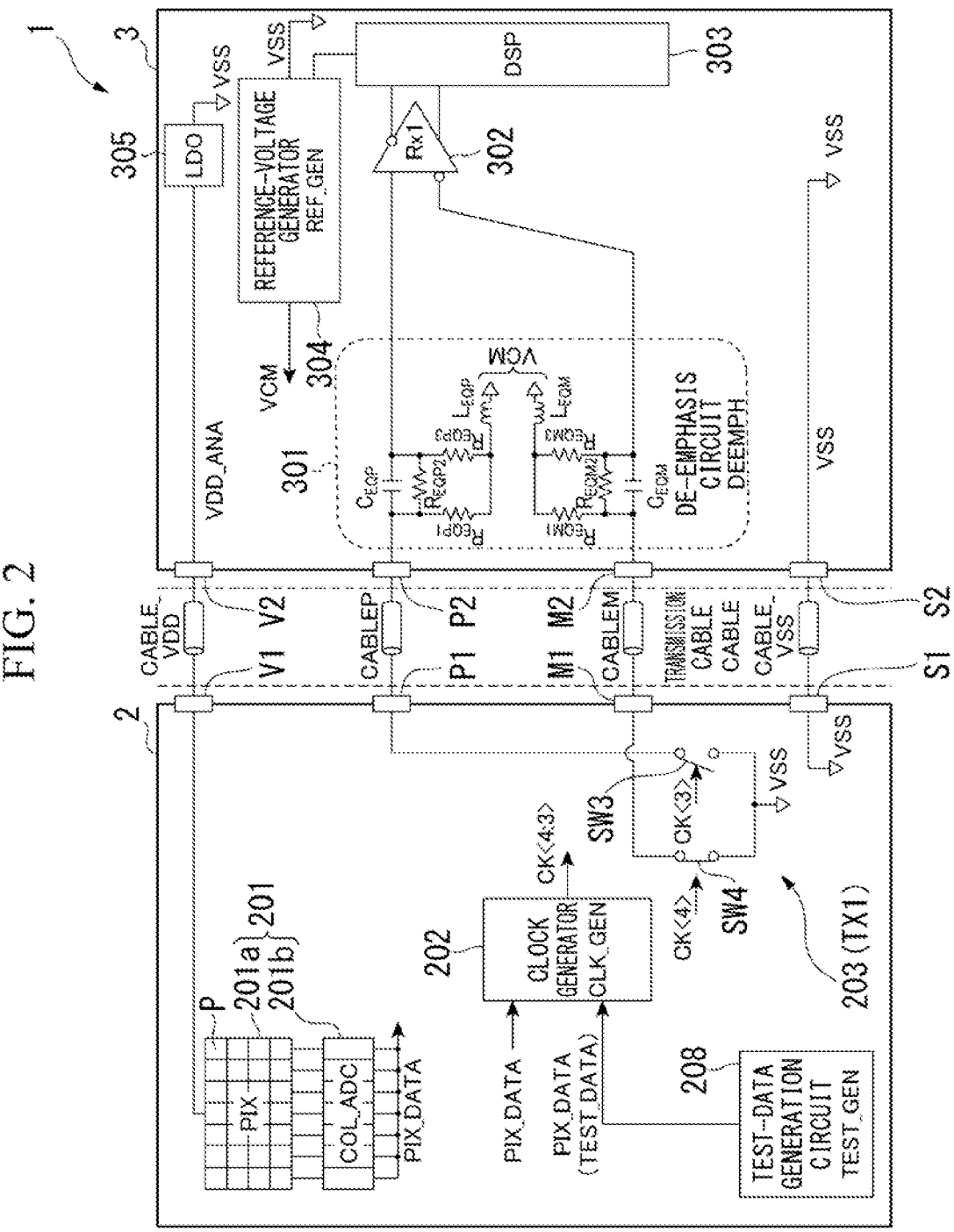
FIG. 2 is a block diagram showing an example of a configuration of an imaging system according to a first embodiment of the present invention.

FIG. 2 is a block diagram showing an example of a configuration of an imaging system according to a first embodiment of the present invention.

In the imaging system 1, the camera unit 2 (image sensor) and the information-processing unit 3 are connected to each other by a differential-signal transmission line (cables CABLEP and CABLEM), a cable CABLE_VDD, and a cable CABLE_VSS.

<Configuration of Camera Unit 2>

The camera unit 2 shown in FIG. 2 includes a solid-state imaging device 201, a clock generator 202, and an output driver 203. The output driver 203 is shown as Tx1. Hereinafter, the output driver 203 is called an output driver Tx1.

The solid-state imaging device 201 includes a PIX unit 201a (PIX) and a signal-processing circuit 201b (COL_ADC).

The PIX unit 201a includes a plurality of pixels P. In FIG. 2, m×n pixels P are arranged. For example, m is four and n is eight as shown in FIG. 2. In other words, in FIG. 2, m×n unit pixels P, each including a photoelectric conversion element, are two-dimensionally arranged in a matrix shape and constitute the PIX unit 201a including a plurality of pixel arrays. Hereinafter, the unit pixel P is simply called a pixel.

The signal-processing circuit 201b is a so-called column analog-to-digital converter (ADC) that converts an analog signal output from a pixel P into a digital signal while suppressing fixed-pattern noise of the pixel by using analog-to-digital (AD) conversion circuits that perform processing in parallel for each column of the pixels P of the PIX unit 201a. The digital signal generated and output by the signal-processing circuit 201b is shown as imaging data PIX_DATA in FIG. 2. The imaging data PIX_DATA, for example, are shown as imaging data of p bits for each of the pixels P.

The imaging data PIX_DATA and test data PIX_DATA (TEST_DATA) including the imaging data are input to the clock generator 202. Hereinafter, the test data PIX_DATA are called test data TEST_DATA. The clock generator 202 serially outputs data of p bits as a signal CK<3> and a signal CK<4>. The signal CK<3> and the signal CK<4> are mutually exclusive digital signals so that, for example, the signal CK<4> is "01010101" (p indicates eight bits) when the signal CK<3> is "10101010." The signal CK<3> and the signal CK<4> may also be called serial signals in a differential-signal form.

The output driver Tx1 includes a switch SW3 to which the signal CK<3> is input and a switch SW4 to which the signal CK<4> is input. The output driver Tx1 combines these two signals into a pair of differential signals and outputs the pair of differential signals from a pad P1 and a pad M1 to a pair of differential-signal transmission lines (two cables CABLEP and CABLEM). The pair of differential signals are output to the de-emphasis circuit 301 of the information-processing unit 3 through a pad P2 and a pad M2 of the information-processing unit 3 connected to the camera unit 2 by the differential-signal transmission lines.

Here, the switch SW3 is provided between a substrate voltage VSS and the pad P1. When the signal CK<3> is "1," the switch SW3 causes the substrate voltage VSS and the pad P1 to be conductive to each other. When the signal CK<3> is "0," the switch SW3 causes the substrate voltage VSS and the pad P1 not to be conductive to each other. In addition, the switch SW4 is provided between the substrate voltage VSS and the pad M1. When the signal CK<4> is "1," the switch SW4 causes the substrate voltage VSS and the pad M1 to be conductive to each other. When the signal CK<4> is "0," the switch SW4 causes the substrate voltage VSS and the pad M1 not to be conductive to each other.

For example, a case is assumed in which the de-emphasis circuit 301 (DEEMPH) described later, which functions as a power supply source to the output driver Tx1, supplies the output driver Tx1 with the voltage of 1 V as a reference voltage VCM. When the signal CK<3> is "0" and the signal CK<4> is "1," the voltage of the pad P1 is 1 V and the voltage of the pad M1 is 0 V. On the other hand, when the signal CK<3> is "1" and the signal CK<4> is "0," the voltage of the pad P1 is 0 V and the voltage of the pad M1 is 1 V. In other words, the amplitude of the differential signal output by the output driver Tx1 is 1 V when the differential signal is expressed as a single-ended form and the amplitude is 2 V when the differential signal is expressed as a differential-signal form. A detailed operation will be described after the de-emphasis circuit 301 is described.

<Configuration of Information-Processing Unit 3>

The information-processing unit 3 includes the de-emphasis circuit (DEEMPH) 301, a receiver 302, the DSP 303 (error determination unit), the reference-voltage generator 304 (voltage generator), and a low dropout (LDO) 305. The receiver 302 is shown as Rx1. Hereinafter, the receiver 302 is called a receiver Rx1.

The LDO 305 steps down a predetermined direct-current (DC) voltage and supplies a DC power source voltage VDD (VDD_ANA) that has been stepped down to the solid-state imaging device 201 of the camera unit 2 through a path passing through a pad V2, the cable CABLE_VDD, and a pad V1. The substrate voltage VSS is supplied to the camera unit 2 through a path passing through a pad S2, the cable CABLE_VSS, and a pad S1.

The reference-voltage generator 304 (voltage generator) steps down the power source voltage VDD stepped down by the LDO 305 in accordance with an instruction from the DSP 303, generates the reference voltage VCM, and supplies the de-emphasis circuit 301 with the generated reference voltage VCM.

The receiver Rx1 is a circuit for binarizing the imaging data PIX_DATA and the test data PIX_DATA (TEST_DATA) including the imaging data received as a differential amplification signal by the pad P2 and the pad M2.

The DSP 303 processes the binarized imaging data PIX_DATA. This processing includes processing of converting the imaging data PIX_DATA on which gradation correction or the like has been performed into a format that the monitor 30 is able to display. The monitor 30 is shown in FIG. 1, but is not shown in FIG. 2.

The processing of the binarized test data TEST_DATA will be described in detail in a second embodiment of the present invention.

The de-emphasis circuit 301 includes a capacitance element $C_{EQP}$, a resistance element $R_{EQP2}$, a resistance element $R_{EQP1}$, a resistance element $R_{EQP3}$, a coil $L_{EQP}$, a capacitance element $C_{EQM}$, a resistance element $R_{EQM2}$, a resistance element $R_{EQM1}$, a resistance element $R_{EQM3}$, and a coil $L_{EQM}$.

One end of the capacitance element $C_{EQP}$ is connected to the pad P2 and the other end of the capacitance element $C_{EQP}$ is connected to the non-inverting input terminal of the receiver Rx1.

One end of the resistance element $R_{EQP2}$ is connected to the pad P2 and the other end of the resistance element $R_{EQP2}$ is connected to the non-inverting input terminal of the receiver Rx1 as with the capacitance element $C_{EQP}$.

One end of the resistance element $R_{EQP1}$ is connected to one end of the resistance element $R_{EQP2}$ and the other end of the resistance element $R_{EQP1}$ is connected to the other end of the coil $L_{EQP}$.

One end of the resistance element $R_{EQP3}$ is connected to the other end of the resistance element $R_{EQP2}$ and the other end of the resistance element $R_{EQP3}$ is connected to the other end of the coil $L_{EQP}$.

The reference voltage VCM is input to one end of the coil $L_{EQP}$.

In addition, one end of the capacitance element $C_{EQM}$ is connected to the pad M2 and the other end of the capacitance element $C_{EQM}$ is connected to the inverting input terminal of the receiver Rx1.

One end of the resistance element $R_{EQM2}$ is connected to the pad M2 and the other end of the resistance element $R_{EQM2}$ is connected to the inverting input terminal of the receiver Rx1 as with the capacitance element $C_{EQM}$.

One end of the resistance element $R_{EQM1}$ is connected to one end of the resistance element $R_{EQM2}$ and the other end of the resistance element $R_{EQM1}$ is connected to the other end of the coil $L_{EQM}$.

One end of the resistance element $R_{EQM3}$ is connected to the other end of the resistance element $R_{EQM2}$ and the other end of the resistance element $R_{EQM3}$ is connected to the other end of the coil $L_{EQM}$.

The reference voltage VCM is input to one end of the coil $L_{EQM}$.

According to the above-described configuration, the de-emphasis circuit 301 functions as an amplitude controller that controls the amplitude of the differential signal output by the output driver 203 by using the substrate voltage VSS and the reference voltage VCM higher than the substrate voltage VSS and lower than the power source voltage VDD while functioning as the equalizer disclosed in Japanese Unexamined Patent Application, First Publication No. 2018-094235.

In other words, the de-emphasis circuit 301 of the information-processing unit 3 shown in FIG. 2 is able to supply the output driver Tx1 of the camera unit 2 with all or part of the energy necessary for generating a pair of differential signals output by the output driver Tx1 through digital signal lines connected to the de-emphasis circuit 301. The digital signal lines are differential-signal transmission lines (cables CABLEP and CABLEM). Thus, by providing the camera unit 2 in which the output driver Tx1 is mounted, the reference voltage VCM lower than the power source voltage VDD can be supplied to the output driver Tx1 without adding a dedicated power source line. Therefore, the power consumption of the output driver Tx1 can be reduced while the signal quality is maintained.

In the first embodiment shown in FIG. 2, the reference voltage VCM is input from the input terminal (one ends of the coil $L_{EQP}$ and coil $L_{EQM}$) of the de-emphasis circuit (DEEMPH) 301. This voltage functions as a power supply source of the output driver Tx1.

Here, the amplitude of the voltage output by the output driver Tx1 is given as the difference between the reference voltage VCM and the voltage "(VCM−VSS)×($R_{ON}$/($R_{ON}$+$R_{CABLE}$+$Z_{EQP, M}$))." When the substrate voltage VSS is zero, the actual difference (amplitude) is expressed as "VCM×{1−($R_{ON}$/($R_{ON}$+$R_{CABLE}$+$Z_{EQP, M}$))}."

In the above-described expression, $R_{ON}$ indicates the on-resistance of the switch SW3 and the switch SW4, that is, the on-resistance when the signal CK<3> or the signal CK<4> is "1" and the switch SW3 or the switch SW4 is conductive. In addition, $R_{CABLE}$ indicates the resistance of the differential-signal transmission lines (cables CABLEP and CABLEM). In addition, $Z_{EQP, M}$ indicates the impedance of the de-emphasis circuit 301.

Therefore, in a case in which the condition "$R_{ON}=R_{CABLE}+Z_{EQP, M}=50\Omega$" is met and the reference voltage VCM is 700 mV, the same signal amplitude as that in a low-voltage differential-signaling (LVDS) driver of the prior art is obtained. In LVDS standards, the amount of current flowing in a circuit is 3.5 mA. In a case in which the termination resistance is 100Ω, in other words, termination resistors of 50Ω are connected in series on the positive side and the negative side, the amplitude of 350 mV expressed as a single-ended form or the amplitude of 700 mV expressed as a differential-signal form is obtained.

The power consumption in the camera unit 2 necessary for that operation is only the loss in the voltage drop occurring in the switch SW3 or the switch SW4 and is given as the following expression. As shown in the following expression, the power consumption can be substantially reduced, compared to the calculation in an LVDS driver for which the amount of current flowing in a circuit is 3.5 mA.

$$P=V^2/R_{ON}=(0.7/2)^2/50 \text{ W}=2.45 \text{ mW}$$

Here, in the above-described expression, V is a value of the voltage calculated as VCM/2 and is given by "V={$R_{ON}$/($R_{ON}$+$R_{CABLE}$+$Z_{EQP,M}$)}×VCM=VCM/2."

In addition, according to the calculation in an LVDS driver for which the amount of current flowing in a circuit is 3.5 mA, the amount of heat generation in the camera unit 2 supplying the output current of the LVDS driver (output driver corresponding to the output driver Tx1) of the camera unit 2 reaches 11.55 mW as indicated by the following expression in a case in which the voltage of about VDD=3.3 V necessary for maintaining the imaging performance of a pixel unit (PIX unit 201a) is supplied as the reference voltage VCM.

$$P=I\times V=3.5 \text{ mA}\times 3.3 \text{ V}=11.55 \text{ mW}$$

Therefore, by supplying the energy necessary for generating a pair of differential signals output by the output driver Tx1 of the camera unit 2 through digital signal lines (differential-signal transmission lines (cables CABLEP and CABLEM)) connected to the de-emphasis circuit 301 of the information-processing unit 3, the power consumption of the output driver Tx1 can be reduced while the signal quality is maintained without adding a power source line for supplying the output driver Tx1 with the reference voltage VCM lower than the power source voltage VDD.

In other words, the imaging system 1 of the embodiment can reduce the number of lines in the scope 10 and can reduce the power consumption.

Second Embodiment

Next, a second embodiment of the present invention will be described with reference to FIG. 1 again.

In the second embodiment, the information-processing unit 3 is able to connect to or communicate with an external treatment device. The information-processing unit 3 sets the reference voltage VCM generated by the reference-voltage generator 304 when the external treatment device is operating (hereinafter, a second operation mode) to be higher than the reference voltage VCM when the external treatment device is not operating (hereinafter, a first operation mode).

Here, the "external treatment device" means various kinds of treatment tools including an ultrasonic coagulation-and-incision apparatus such as an ultrasonic scalpel, a high-frequency current generator such as an electric scalpel, and the like. In addition, channels are provided for the purpose of passing from the operation unit 14 to the insertion unit 11 shown in FIG. 1. The channels cause the "external treatment device" to pass through to the distal end of the insertion unit 11. With these channels provided, observation using an endoscope (camera unit 2) and treatment using treatment tools can be simultaneously performed.

In addition, the "first operation mode" means an operation in an imaging mode using the camera unit 2 when the "external treatment device" is not operating and the "second operation mode" means an operation in a treatment mode when the "external treatment device" is operating.

The camera unit 2 includes a test-data generation circuit 208 that outputs test data having a predetermined pattern of data. The camera unit 2 is able to operate in a third operation mode for outputting the imaging data PIX_DATA and the second operation mode for outputting the predetermined test data TEST_DATA. In addition, the DSP 303 in the information-processing unit 3 outputs, to the reference-voltage generator 304, an instruction signal for controlling the reference voltage VCM output by the reference-voltage generator 304 in accordance with the error rate of the test data TEST_DATA binarized by the receiver Rx1.

The third operation mode and the second operation mode are switched between in turns. When the error rate of the test data TEST_DATA received by the receiver Rx1 in a period of the second operation mode is greater than a predetermined value, the DSP 303 outputs, to the reference-voltage generator 304, a control signal (instruction signal) that causes the reference voltage VCM output by the reference-voltage generator 304 to increase. In addition, the reference-voltage generator 304 outputs the reference voltage VCM having a first voltage value VCM1 in the third operation mode and outputs the reference voltage VCM having a second voltage value VCM2 higher than the first voltage value VCM1 in the second operation mode.

In other words, the information-processing unit 3 includes the DSP 303 (error determination unit) that determines an error of the test data TEST_DATA transmitted by the test-data generation circuit 208 and changes the reference voltage VCM generated by the reference-voltage generator 304 in accordance with the results of determining the error. In addition, the DSP 303 (error determination unit) of the information-processing unit 3 sets the reference voltage VCM generated by the reference-voltage generator 304 (voltage generator) to a high voltage when the error rate is greater than the predetermined value.

In this way, in the imaging system 1 in the embodiment, by using the reference voltage VCM having the second voltage value VCM2 in the operation of the treatment mode (second operation mode) in which disturbance noise increases, the amplitude of the imaging data can be temporarily increased. Therefore, data transfer that suppresses the transmission error can be realized while an increase in the amount of heat generated in the image sensor is minimized.

Third Embodiment

Figure 3:
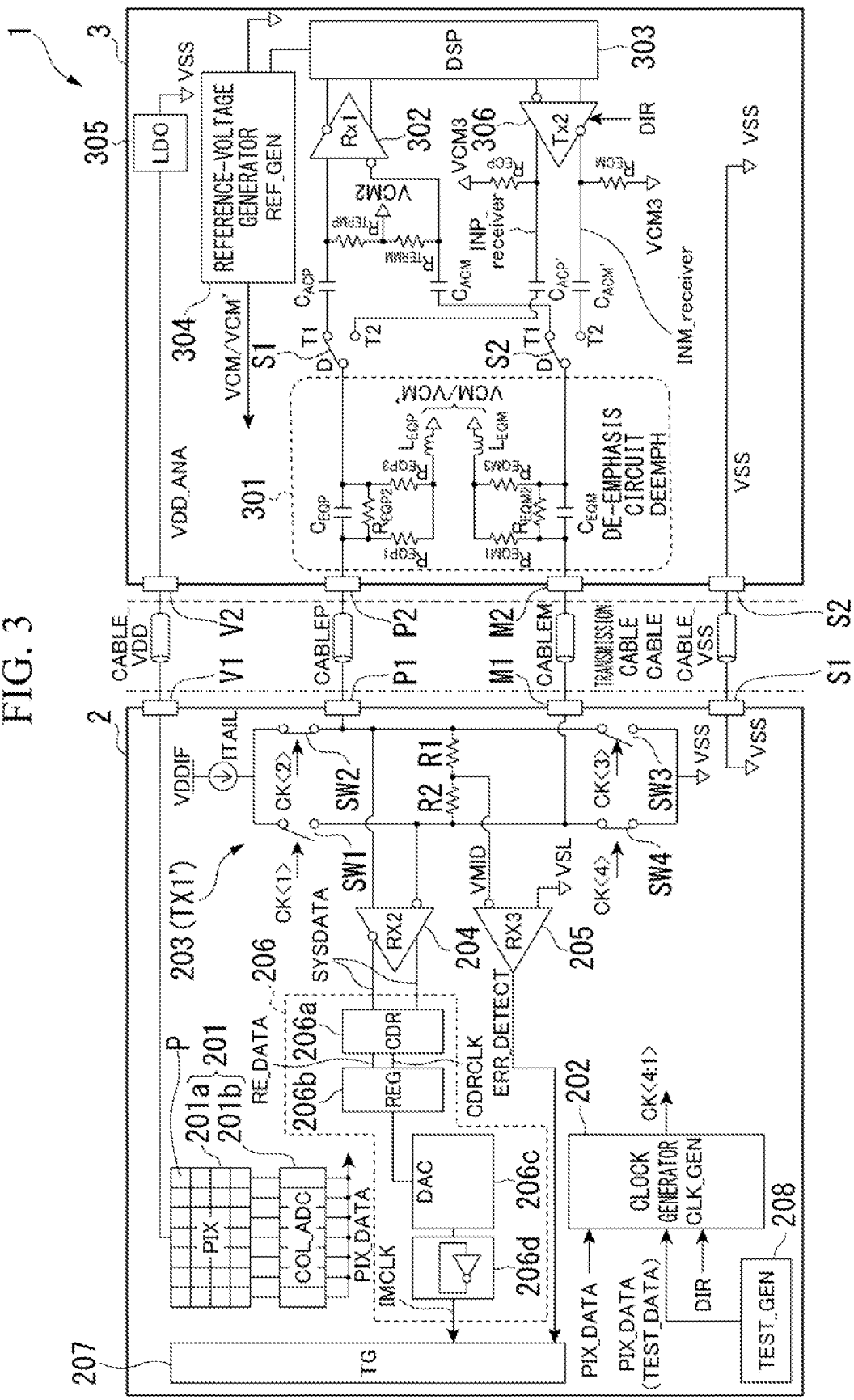
FIG. 3 is a block diagram showing an example of a configuration of an imaging system according to a third embodiment of the present invention.

Next, a third embodiment of the present invention will be described with reference to FIG. 3 and FIG. 4. FIG. 3 is a block diagram showing an example of a configuration of an imaging system according to the third embodiment of the present invention. In addition, FIG. 4 is a timing chart showing an operation of the imaging system according to the third embodiment of the present invention.

FIG. 3 indicates a block diagram of a two-way differential communication circuit. Here, the "two-way differential communication" means two-way communication using a differential signal in a downlink communication mode and an uplink communication mode. The receiver Rx1 in the information-processing unit 3 receives a differential signal transmitted by the output driver 203 in the camera unit 2 shown in FIG. 3 in the downlink communication mode. The receiver 204 in the camera unit 2 receives a differential signal transmitted by the output driver 306 in the information-processing unit 3 in the uplink communication mode.

The output driver 203 is shown as Tx1' in FIG. 3. Hereinafter, the output driver 203 is called an output driver Tx1'. The output driver 306 is shown as Tx2 in FIG. 3. Hereinafter, the output driver 306 is called an output driver Tx2. The receiver 204 is shown as Rx2 in FIG. 3. Hereinafter, the receiver 204 is called a receiver Rx2.

Figure 4:
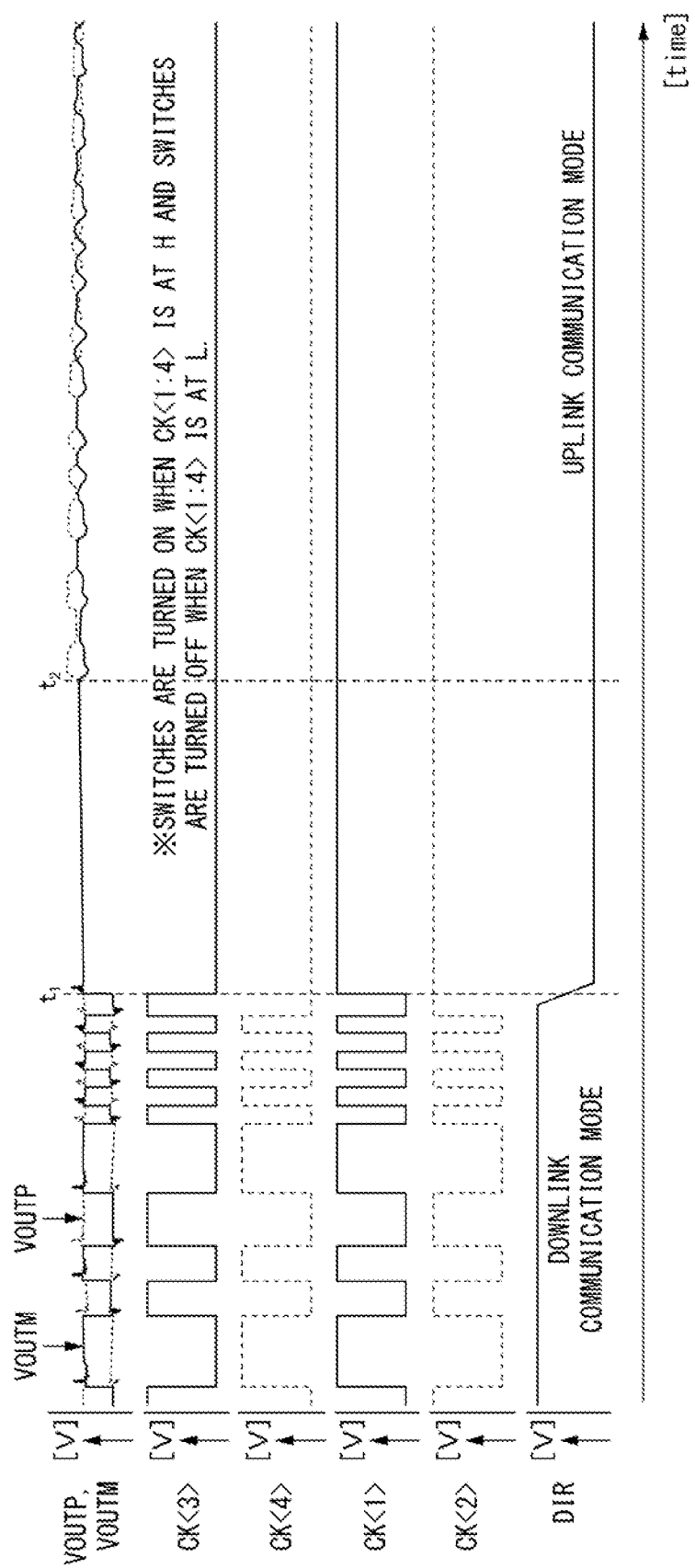
FIG. 4 is a timing chart showing an operation of the imaging system according to the third embodiment of the present invention.

FIG. 4 shows the results of the simulation of a transient response in the two-way communication. VOUTP and VOUTM shown in FIG. 4 indicate a differential signal in the pad P1 of the camera unit 2 and a differential signal in the pad M1 of the camera unit 2, respectively.

In FIG. 3, the same reference numerals are given or the reference signs including characters and the same numbers are given to the same or corresponding configuration shown in FIG. 1 and a description is omitted accordingly.

As shown in FIG. 4, in a period of the downlink communication mode, the states of switches SW1 to SW4 included in the output driver Tx1' are intermittently switched between on the basis of clocks CK<1> to CK<4>.

In addition, in a period of the uplink communication mode, the switches SW3 and SW4 are turned off, and the switches SW1 and SW2 are maintained to be turned on and function as a termination resistor of the receiver Rx2. At the same time, the switches SW1 and SW2 have resistance values of approximately 50Ω, perform the same operation as that of the resistors $R_{TERMP}$ and $R_{TERMN}$ connected to the input end of the receiver Rx1, and form a returning current path for the output driver Tx2.

When the communication mode is switched from the downlink communication mode to the uplink communication mode shown in FIG. 4 at a time point t1, switching of VOUTP and VOUTM is stopped. Here, in FIG. 4, communication directions are controlled on the basis of DIR in order to simplify the description. In fact, data for reporting completion of data communication are included at the end of an uplink signal and a downlink signal, and actual communication directions are changed when the information-processing unit 3 or the camera unit 2 receives the data.

Transmission of a signal from the output driver Tx2 is started at the time point t1 and the signal at this node is stable until a time point t2 at which the signal reaches the receiver Rx2. When the signal from the output driver Tx2 reaches the receiver Rx2 at the time point t2, switching waveforms appear again in a VOUTP terminal and a VOUTM terminal. The VOUTP terminal and the VOUTM terminal are indicated by the pad P1 and the pad M1 in FIG. 3, respectively.

In the imaging system 1 shown in FIG. 3, the reference-voltage generator 304 supplies the de-emphasis circuit 301 with the reference voltage (VCM or VCM') so that the de-emphasis circuit 301 operates in both the "normal operation mode" and the "error reporting mode." The de-emphasis circuit 301 operates in the normal operation mode on the basis of a sufficient amplitude of the signal output by the output driver Tx1' capable of adjusting the amplitude of the output signal. The de-emphasis circuit 301 operates in the error reporting mode on the basis of a lower amplitude of the signal output by the output driver Tx1' than that in the normal operation mode. The lower amplitude may be zero. In this way, resetting of the camera unit 2 having a high degree of freedom can be realized without turning off the power source.

Here, the reference voltage VCM has the first voltage value VCM1 (predetermined value) described in the first and second embodiments. In addition, the reference voltage VCM' has a lower voltage value than the first voltage value VCM1. The de-emphasis circuit DEEMPH outputs a signal indicating an error notification and the DSP 303 sets the output of the reference-voltage generator 304 to VCM' in the "downlink communication mode." When the output of the reference-voltage generator 304 is set to VCM' in the "uplink communication mode," the camera unit 2 is reset. In other words, the reference voltage VCM' has a voltage value making such two-way communication available in the imaging system 1. Details of the downlink communication mode and the uplink communication mode will be described later. This is because comparison processing is executed under the condition that a slice voltage VSL used for the comparison processing by the common-mode detector 205 described later meets the following expression. The common-mode detector 205 is shown as Rx3. Hereinafter, the common-mode detector 205 is called a common-mode detector Rx3.

(Reference voltage $VCM'$)=(slice voltage $VSL$)×2<
(first voltage value $VCM1$)

Details of the comparison processing will be described later.

In order to realize the operations described above, the clock generator 202, the output driver Tx1', and the common-mode detector Rx3 include the following configuration.

The clock generator 202 operates in the "normal operation mode" and the "downlink communication mode" in the "error reporting mode." The imaging data PIX_DATA, the test data PIX_DATA (TEST_DATA) including the imaging data, and a communication-direction control signal DIR are input to the clock generator 202 and the clock generator 202 serially outputs data of p bits as signals CK<1> to CK<4>. The signal CK<3> and the signal CK<4> are mutually exclusive digital signals, and the signal CK<1> and the signal CK<2> are mutually exclusive digital signals so that, for example, the signal CK<4> and the signal CK<2> are "01010101" (p indicates eight bits) when the signal CK<3> and the signal CK<1> are "10101010." The signals may also be called serial signals in a differential-signal form.

The communication-direction control signal DIR includes data for reporting completion of data communication at the end of an uplink signal and a downlink signal, and actual communication directions are changed when the information-processing unit 3 or the camera unit 2 receives the data, as described above. In the embodiment, the clock generator 202 outputs the communication-direction control signal DIR shown in FIG. 4, thus transmitting a signal indicating the uplink or downlink communication direction to the information-processing unit 3.

The output driver Tx1' shown in FIG. 3 includes a tail current source ITAIL connected to a voltage VDDIF, a switch SW1 to which the signal CK<1> is input, a switch SW2 to which the signal CK<2> is input, a switch SW3 to which the signal CK<3> is input, and a switch SW4 to which the signal CK<4> is input.

The output driver Tx1' operates in the "normal operation mode" and also operates in both the "downlink communication mode" and the "uplink communication mode" in the "error reporting mode."

In the "downlink communication mode," the output driver Tx1' combines four signals output by the clock generator 202 into a pair of differential signals and outputs the pair of differential signals from the pad P1 and the pad M1 to a pair of differential-signal transmission lines (two cables CAB-LEP and CABLEM) as with the first embodiment. The pair of differential signals are output to the de-emphasis circuit 301 of the information-processing unit 3 through the pad P2 and the pad M2 of the information-processing unit 3 connected to the camera unit 2 by the differential-signal transmission lines.

On the other hand, in the "uplink communication mode," the switches SW1 and SW2 are turned on when the switches SW3 and SW4 are turned off as described in the first embodiment. Therefore, the output driver Tx1' functions as a termination resistor so that the switches SW1 and SW2 receive signals from the output driver Tx2. At the same time, the output driver Tx1' functions as an element for securing a path of a returning current for the output driver Tx2. Accordingly, the pair of differential signals output from the output driver Tx2 are correctly received by the receiver Rx2 and are output to the imager-clock generation unit 206. The signal SYSDATA output from the receiver Rx2 will be described in detail later. The signal SYSDATA is received data of the camera unit 2.

The common-mode detector Rx3 is a circuit that determines whether or not the signal output from the de-emphasis circuit DEEMPH of the information-processing unit 3 indicates an error notification in the "downlink communication mode" with a resistance element R1 and a resistance element R2 shown in FIG. 3. The common-mode detector Rx3 outputs an error detection flag ERR_DETECT to a timing generator TG in accordance with the result of the determination.

The de-emphasis circuit DEEMPH outputs the signal indicating the error notification in the event that a problem of imaging occurs when the DSP 303 executes the processing of converting the image data into a format that the monitor 30 is able to display. The problem indicates that all the gradation is dark or bright in the imaging data PIX_DATA. In this case, the output of the reference-voltage generator 304 is changed from VCM1 (predetermined value) to VCM' (value including 0 V) that is a value less than VCM1 on the basis of the instruction from the DSP 303.

Each of the resistance element R1 and the resistance element R2 includes one end and the other end. One end of the resistance element R1 is connected to the pad P1 and the other end of the resistance element R1 is connected to the other end of the resistance element R2. One end of the resistance element R2 is connected to the pad M1 and the other end of the resistance element R2 is connected to the other end of the resistance element R1. In other words, the resistance element R1 and the resistance element R2 output a medium voltage VMID from a connection point of the resistance elements to a first input terminal (inverting input terminal) of the common-mode detector Rx3. The medium voltage VMID is the center of the voltage of the pad P1 and the voltage of the pad M1. The connection point constitutes the other end of the resistance element R1 and the other end of the resistance element R2. The voltage of the pad P1 and the voltage of the pad M1 constitute the voltage of the pair of differential signals. The medium voltage VMID indicates the center of the voltage of one of the differential-signal transmission lines and the voltage of the other of the differential-signal transmission lines.

In other words, the circuit, which is constituted by the resistance element R1 and the resistance element R2 and outputs the medium voltage VMID to the common-mode detector Rx3, is called a medium-voltage measurement circuit.

In addition, the common-mode detector Rx3 is a comparator circuit. The slice voltage VSL is input to a second input terminal (non-inverting input terminal) of the common-mode detector Rx3. The common-mode detector Rx3 compares the medium voltage VMID with the slice voltage VSL, performs determination, and outputs the error detection flag ERR_DETECT.

Here, an operation of the common-mode detector Rx3 will be described.

The common-mode detector Rx3 is designed for the purpose of comparing the slice voltage VSL set to a value greater than VSS=0 and less than 0.5×VCM1 with the medium voltage VMID. The error detection flag ERR_DETECT is changed from "L" to "H" when the slice voltage VSL becomes greater than the medium voltage VMID.

Since the medium voltage VMID is expressed as "0.5× VCM1" in the "normal operation mode" in which the reference voltage VCM is set to VCM1, the error detection flag ERR_DETECT is "L." On the other hand, in the "error reporting mode" in which the reference voltage VCM is set to 0, the medium voltage VMID becomes 0 and the error detection flag ERR_DETECT is changed to "H."

In addition, when the slice voltage VSL is set in a range expressed as "0<VSL<0.5×VCM1," the above is realized for any value of $R_{ON}$ and the effects described above can be obtained. In other words, the above-described expression is expressed as "0<reference voltage VCM'=slice voltage VSL×2<voltage value VCM1." Therefore, the camera unit 2 can determine that the reference voltage VCM is reduced to be the value VCM' less than the predetermined value VCM1. Also, the common-mode detector Rx3 can determine that the medium voltage VMID is less than a first predetermined value "0.5×VCM1" corresponding to the predetermined value VCM1 and the slice voltage VSL matches "reference voltage VCM'×0.5."

In other words, the output of the reference-voltage generator 304 is set to VCM1 (predetermined value) when normal communication is performed and the output of the reference-voltage generator 304 is set to VCM' (including 0 V) less than VCM1 when the operation of the camera unit 2 needs to be changed on the basis of the error notification. The operation of the camera unit 2 is changed to a resetting operation or an error-recovery operation described later. In this way, resetting of the camera unit 2 having a high degree of freedom can be realized.

Next, a detailed configuration and operation of the imager-clock generation unit 206 included in the camera unit 2 shown in FIG. 3 will be described with reference to FIG. 5 and FIG. 6.

Figure 5:
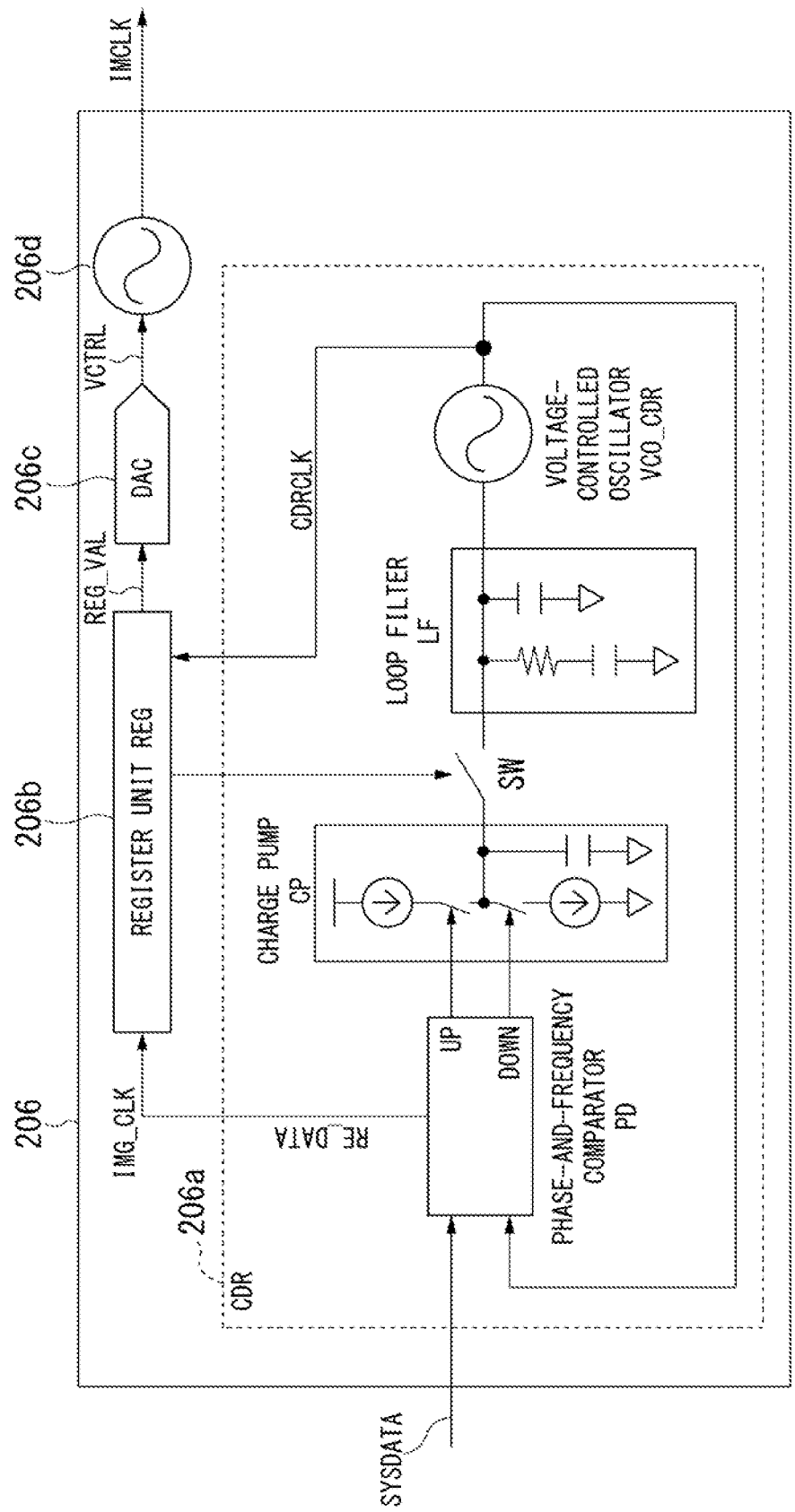
FIG. 5 is a diagram showing a configuration of an imager-clock generation unit IMG_CLK shown in FIG. 3.

FIG. 5 is a diagram showing a configuration of the imager-clock generation unit 206 shown in FIG. 3. In addition, FIG. 6 is a timing chart showing a logical state of a major node of the imager-clock generation unit 206 shown in FIG. 3.

The imager-clock generation unit 206 includes a clock-data recovery unit 206a, a register unit 206b, a digital-to-analog convertor 206c, and a voltage-controlled oscillator 206d. Hereinafter, the voltage-controlled oscillator 206d is called a voltage-controlled oscillator VCO_IMCLK.

The imager-clock generation unit 206 is shown as IMG_CLK in FIG. 5. Hereinafter, the imager-clock generation unit 206 is called an imager-clock generation unit IMG_CLK. In addition, the clock-data recovery unit 206a is shown as CDR in FIG. 5. Hereinafter, the clock-data recovery unit 206a is called a clock-data recovery unit CDR. In addition, the register unit 206b is shown as REG in FIG. 5. Hereinafter, the register unit 206b is called a register unit REG In addition, the digital-to-analog convertor 206c is shown as DAC in FIG. 5. Hereinafter, the digital-to-analog convertor 206c is called a digital-to-analog convertor DAC.

The voltage-controlled oscillator VCO_IMCLK outputs an imager clock IMCLK to the timing generator TG The imager clock IMCLK oscillates at a frequency in accordance with a control voltage VCTRL input to the voltage-controlled oscillator VCO_IMCLK. The timing generator TG is shown as the TG 207 in FIG. 3. Thus, the camera unit 2 performs an operation synchronized with the imager clock IMCLK.

The digital-to-analog convertor DAC outputs the control voltage VCTRL (analog signal) in accordance with a register value REG_VAL (digital signal) input to the digital-to-analog convertor DAC.

Register data RE_DATA are input to the register unit REG in synchronization with a CDR clock CDRCLK input from the clock-data recovery unit CDR and the value of the register data RE_DATA is held in the register unit REG The reception data SYSDATA are input to the imager-clock generation unit IMG_CLK. The reception data SYSDATA include a clock-recovery symbol for each predetermined cycle. The clock-recovery symbol includes clock edges for detecting timings at which data change. In general, 8b/10b, a Manchester-encoded signal, and the like are known as the reception data SYSDATA.

Figure 6:
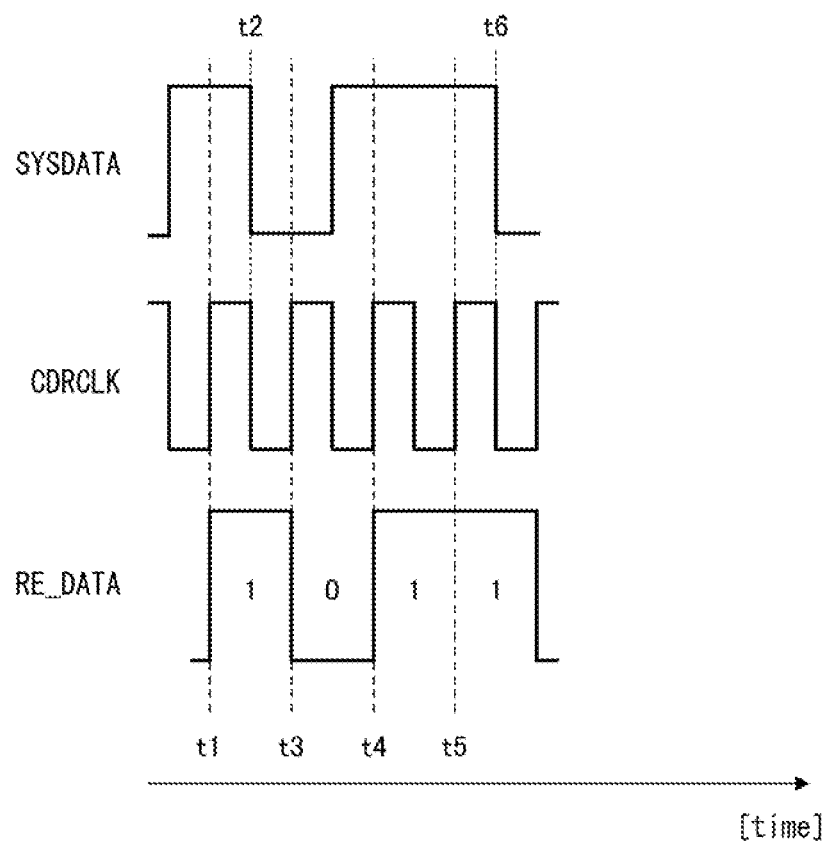
FIG. 6 is a timing chart showing a logical state of a major node of the imager-clock generation unit IMG_CLK shown in FIG. 3.

The clock-data recovery unit CDR executes phase adjustment so that the phase of the reception data SYSDATA matches the phase of a falling clock of the CDR clock CDRCLK (see lines at time points t2 and t6 in FIG. 6).

A phase-and-frequency comparator PD in the clock-data recovery unit CDR samples a value of the reception data SYSDATA at timings of rising edges of the CDR clock CDRCLK (see lines at time points t1, t3, t4, and t5 in FIG. 6) and outputs re-timing data RE_DATA synchronized with the CDR clock CDRCLK to the register unit REG The data held in the register unit REG is used for setting an operation mode or the like in the camera unit 2.

Here, an operation of switching between communication directions will be described.

A system-line completion command (for example, "1011") is transmitted from the information-processing unit 3 and this value is detected as the re-timing data RE_DATA. At this time, the communication mode is changed to the downlink communication mode (time points 0 to t1 in FIG. 4) and the camera unit 2 outputs a digital video signal (imaging data PIX_DATA) to the information-processing unit 3.

When the downlink communication mode is started, the switch SW shown in FIG. 5 is turned off and the voltage in the loop filter LF is maintained. Therefore, the voltage supplied to the voltage-controlled oscillator VCO_CDR in the period of the downlink communication mode is fixed and the frequency of the CDR clock CDRCLK in the period is fixed.

The camera unit 2 outputs an imager-line completion command (for example, "0100") to the system after outputting a digital video signal (imaging data PIX_DATA) of one line to the information-processing unit 3. Thereafter, the communication mode is changed to the uplink communication mode again.

In the uplink communication mode, the switch SW is short-circuited again, and an operation of frequency lock (re-adjustment) of the CDR clock CDRCLK and an operation of extracting the reception data SYSDATA are executed on the basis of the reception data SYSDATA.

The TG 207 (timing generator TG) shown in FIG. 3, for example, executes the resetting operation or the error-recovery operation described below. In other words, the TG 207 measures the length of a period during which the common-mode detector Rx3 outputs the error detection flag ERR-DETECT on the basis of the imager clock IMCLK output by the imager-clock generation unit 206. In this way, the TG 207 executes the resetting operation or the error-recovery operation depending on the length of a period during which the error detection flag ERR_DETECT is "H" as shown in the following examples (1) to (4).

(1) When the length of the period during which the error detection flag ERR_DETECT is "H" corresponds to a reading period for one line, the TG 207 may execute skip-reading of two lines. The reading period is indicated by the number of clocks of the imager clock IMCLK for one line.

(2) When the length of the period during which the error detection flag ERR_DETECT is "H" corresponds to a reading period for two lines, the TG 207 may initialize a value of a predetermined counter in the TG 207.

(3) When the length of the period during which the error detection flag ERR_DETECT is "H" corresponds to a reading period for three lines, the TG 207 may initialize a value of an on-chip register REG (register unit 206*b*).

(4) When the length of the period during which the error detection flag ERR_DETECT is "H" corresponds to a reading period for four lines, the operation of the camera unit 2 may be changed to a communication-training phase.

In other words, the error determination unit (DSP 303) of the information-processing unit 3 reduces the reference voltage VCM to be a value (VCM') less than a predetermined value (VCM1) when the error determination unit determines that an error has occurred under a predetermined condition in the imaging data (PIX_DATA) transmitted by the solid-state imaging device 201. As a result of this, the camera unit 2 determines that the reference voltage VCM is reduced to be a value less than the predetermined value (VCM1) and executes the resetting operation or the error-recovery operation. In addition, the camera unit 2 includes the medium-voltage measurement circuit (resistance elements R1 and R2) that measures the medium voltage VMID of the differential-signal transmission lines. The camera unit 2 executes the resetting operation or the error-recovery operation when the medium voltage VMID is less than the first predetermined value (0.5×VCM1) corresponding to the predetermined value (VCM1). In addition, the camera unit 2, that is, the TG 207 in the camera unit 2 determines the contents of the resetting operation or the error-recovery operation in accordance with the length of a predetermined period during which the medium voltage VMID is less than the first predetermined value (0.5×VCM1) corresponding to the predetermined value (VCM1). The predetermined period corresponds to a period during which the error detection flag ERR_DETECT is "H."

In this way, in the imaging system 1 in the embodiment, the number of lines in the scope 10 are reduced and power consumption is reduced. Also, resetting (the resetting operation or the error-recovery operation) of the camera unit 2 having a high degree of freedom can be realized without turning off the power source.

Fourth Embodiment

Next, a fourth embodiment of the present invention will be described with reference to FIG. 7.

Figure 7:
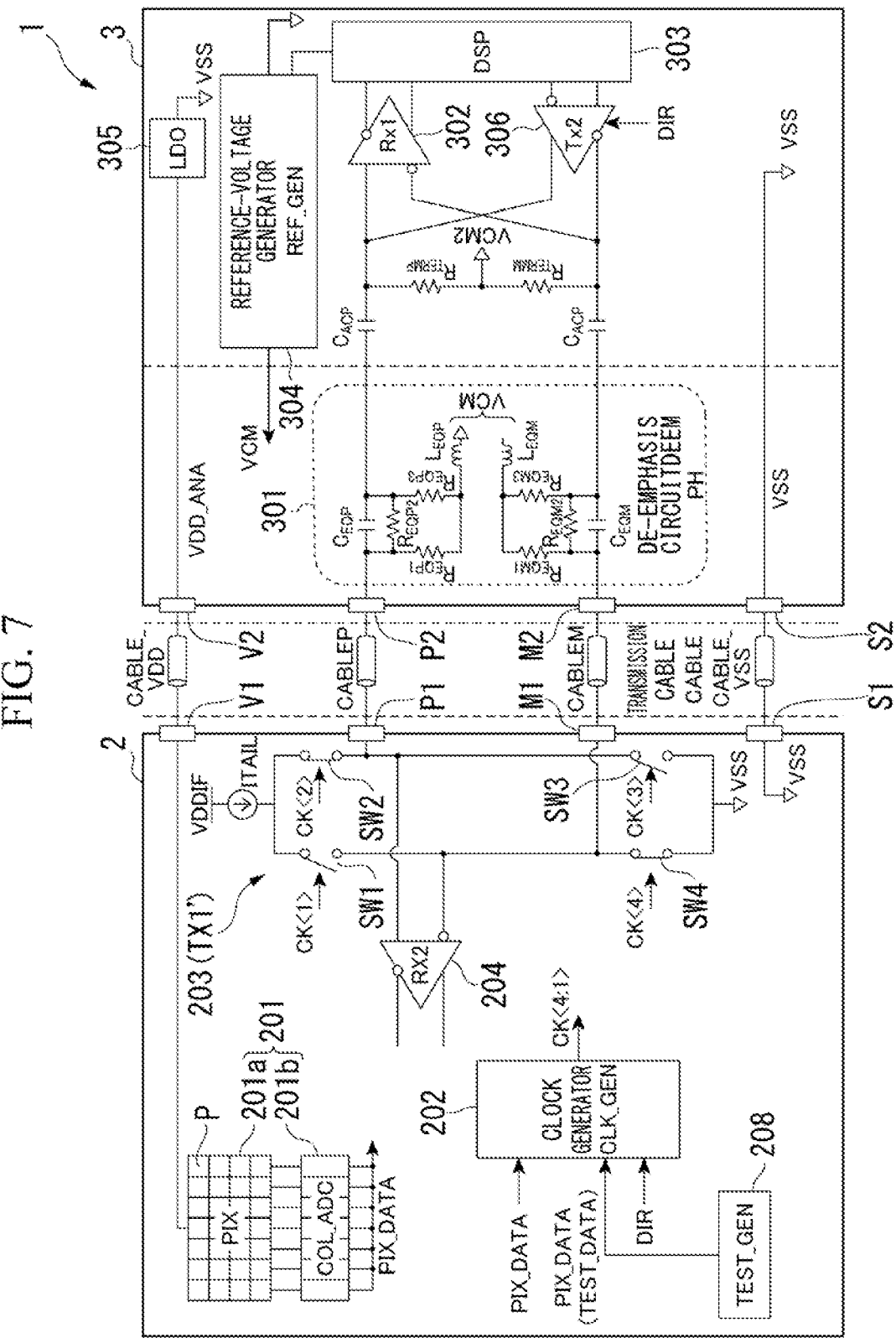
FIG. 7 is a block diagram showing an example of a configuration of an imaging system according to fourth to seventh embodiments of the present invention.

FIG. 7 is a block diagram showing an example of a configuration of an imaging system according to the fourth embodiment of the present invention.

The imaging system 1 is shown in FIG. 7 that schematically shows the imaging system 1 shown in FIG. 3. The same reference numerals are given to the same configuration as that shown in FIG. 3 and a description is omitted accordingly.

The information-processing unit 3 sets the reference voltage VCM generated by the reference-voltage generator 304 (voltage generator) to a first value (predetermined value VCM1) in the downlink communication mode and sets the reference voltage VCM generated by the reference-voltage generator 304 to a second value (VCM2 or VCM') different from the first value in the uplink communication mode.

In this way, the reference voltage VCM in an uplink communication phase can be set to the operation voltage so that the performance of the receiver 204 (receiver Rx2) is the highest. Therefore, the receiver Rx2 reliably operates when high-speed signals are input. In other words, it is also possible to provide an endoscope system (imaging system) that is more robust to disturbance noise than a conventional one.

Fifth Embodiment

Next, a fifth embodiment of the present invention will be described with reference to FIG. 7.

The information-processing unit 3 shown in FIG. 7 is able to connect to or communicate with an external treatment device as with the information-processing unit 3 described in the second embodiment by using FIG. 1. The information-processing unit 3 sets the value of the reference voltage VCM generated by the reference-voltage generator 304 when the external treatment device is operating (second operation mode) to be a voltage value VCM2 higher than a voltage value VCM1 when the external treatment device is not operating (third operation mode).

In this way, by using the reference voltage VCM having the voltage value VCM2 (second voltage value) in the operation of the treatment mode in which disturbance noise increases, the amplitude of the imaging data can be temporarily increased. Therefore, data transfer that suppresses the transmission error can be realized while an increase in the amount of heat generated in the camera unit 2 (image sensor) is minimized.

Sixth Embodiment

Next, a sixth embodiment of the present invention will be described with reference to FIG. 7.

The camera unit 2 includes a temperature sensor (not shown in FIG. 7) that measures the temperature of the camera unit 2. The camera unit 2 transmits the temperature output from the temperature sensor to the information-processing unit 3.

The information-processing unit 3 sets the value of the reference voltage VCM to a value VCM1' (<VCM1) less than VCM1 when the measured temperature is higher than a predetermined temperature. The temperature of the camera unit 2 is influenced by the reference voltage VCM of the de-emphasis circuit. As the reference voltage VCM increases, the temperature of the camera unit 2 also increases and therefore may adversely influence a human body and chip performance. In the embodiment, when the temperature of the camera unit 2 (image sensor) is higher than the predetermined temperature that influences a human body and chip performance, the value of the reference voltage VCM is set to the value VCM1' (<VCM1) less than VCM1.

In this way, the amplitude of the signal transmitted in the downlink communication phase can be increased as long as an adverse influence on a human body and chip performance caused by the temperature of the camera unit 2 (image sensor) is allowed. Therefore, it is possible to provide an endoscope system more robust to disturbance noise than a conventional one.

Seventh Embodiment

Next, a seventh embodiment of the present invention will be described with reference to FIG. 7.

The camera unit 2 shown in FIG. 7 further includes the receiver 204 (reception driver) that receives data from the information-processing unit 3 through the differential-signal transmission lines as with the camera unit 2 described in the third embodiment by using FIG. 3. In addition, the imaging system 1 is able to switch the communication mode from the downlink communication mode of transmitting data from the output driver 203 (Tx1') to the information-processing unit 3 to the uplink communication mode of transmitting data from the information-processing unit 3 to the receiver 204.

The output driver Tx1' includes the switch SW1 (first switch), the switch SW2 (second switch), the switch SW3 (third switch), and the switch SW4 (fourth switch).

The output driver Tx1' simultaneously turns on or off the switch SW1 and the switch SW3 and simultaneously turns on or off the switch SW2 and the switch SW4, thus outputting the imaging data as a differential signal in the downlink communication mode. In other words, the output driver Tx1' simultaneously turns off the switch SW2 and the switch SW4 when the output driver Tx1' simultaneously turns on the switch SW1 and the switch SW3. The output driver Tx1' simultaneously turns on the switch SW2 and the switch SW4 when the output driver Tx1' simultaneously turns off the switch SW1 and the switch SW3. In addition, the output driver Tx1' turns on the switch SW1 and the switch SW2 and turns off the switch SW3 and the switch SW4 in the uplink communication mode, thus forming a transmission path of the differential signal. In this way, the switch SW1 and the switch SW2 become part of the termination resistance in the uplink communication mode.

Since the switch SW1 and the switch SW2 constitute the termination resistance in the uplink communication mode, termination resistance does not need to be provided in the camera unit 2. Therefore, an imaging system (endoscope system) in which the camera unit 2 is miniaturized can be provided.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging system, comprising:
a camera unit; and
an information-processing unit,
wherein the camera unit and the information-processing unit are connected to each other by differential-signal transmission lines,
the camera unit comprises:
a solid-state imaging device configured to operate on the basis of a power source voltage higher than a substrate voltage and generate imaging data; and
an output driver configured to output a differential signal of the imaging data to the differential-signal transmission lines, and
the information-processing unit comprises:
a voltage generator configured to generate a reference voltage higher than the substrate voltage and lower than the power source voltage; and
a de-emphasis circuit configured to control an amplitude of the differential signal by using the substrate voltage and the reference voltage.

2. The imaging system according to claim 1,
wherein the camera unit comprises a test-data generation circuit configured to output test data,
the camera unit is configured to output a differential signal of the test data in addition to the differential signal of the imaging data to the differential-signal transmission lines through the output driver,
the information-processing unit comprises an error determination circuit configured to determine an error of the test data, and
the error determination circuit is configured to change the reference voltage to be generated by the voltage generator in accordance with a determination result of the error.

3. The imaging system according to claim 2,
wherein, the error determination circuit is configured to increase the reference voltage to be generated by the voltage generator when an error rate is greater than a predetermined value.

4. The imaging system according to claim 2,
wherein the error determination circuit is configured to reduce the reference voltage to be a voltage having a value less than a predetermined value when the error determination circuit determines that an error of the imaging data has occurred, and
the camera unit is configured to execute a resetting operation or an error-recovery operation in a case in which the camera unit determines that the reference voltage is reduced to be the voltage having the value less than the predetermined value.

5. The imaging system according to claim 4,
wherein the camera unit comprises a medium-voltage measurement circuit configured to measure a medium voltage of the differential-signal transmission lines, and
the camera unit is configured to execute the resetting operation or the error-recovery operation when the medium voltage is less than a value associated with the predetermined value.

6. The imaging system according to claim 5,
wherein the camera unit is configured to determine contents of the resetting operation or the error-recovery operation in accordance with a length of a period during which the medium voltage is less than the value associated with the predetermined value.

7. The imaging system according to claim 1,
wherein the camera unit further comprises a reception driver configured to receive data from the information-processing unit through the differential-signal transmission lines,
the imaging system is configured to switch between a downlink communication mode of transmitting data from the output driver to the information-processing unit and an uplink communication mode of transmitting data from the information-processing unit to the reception driver, and the information-processing unit is configured to:
- set the reference voltage to be generated by the voltage generator to a first value in the downlink communication mode; and
- set the reference voltage to be generated by the voltage generator to a second value different from the first value in the uplink communication mode.

8. The imaging system according to claim 1,
wherein the information-processing unit is configured to:
- connect to or communicate with an external treatment device; and
- set the reference voltage to be generated by the reference-voltage generator when the external treatment device is operating to be higher than the reference voltage when the external treatment device is not operating.

9. The imaging system according to claim 1,
wherein the camera unit is configured to transmit data including temperature information of the camera unit acquired by a temperature sensor to the information-processing unit, and the information-processing unit is configured to reduce the reference voltage when the measured temperature is higher than a predetermined temperature.

10. The imaging system according to claim 1,
wherein the camera unit further comprises a reception driver configured to receive data from the information-processing unit through the differential-signal transmission lines, the imaging system is configured to switch between a downlink communication mode of transmitting data from the output driver to the information-processing unit and an uplink communication mode of transmitting data from the information-processing unit to the reception driver, the output driver includes a first switch, a second switch, a third switch, and a fourth switch, the output driver is configured to simultaneously turn on or off the first switch and the third switch and simultaneously turn on or off the second switch and the fourth switch so as to output the imaging data as the differential signal in the downlink communication mode, and the output driver is configured to turn on the first switch and the second switch and turn off the third switch and the fourth switch in the uplink communication mode so as to form a transmission path of a differential signal of the data transmitted from the information-processing unit to the reception driver and so as to cause the first switch and the second switch to be part of a termination resistance in the uplink communication mode.

* * * * *